United States Patent [19]
Eggers et al.

[11] Patent Number: 5,480,397
[45] Date of Patent: Jan. 2, 1996

[54] SURGICAL INSTRUMENT WITH AUTO-REGULATING HEATER AND METHOD OF USING SAME

[75] Inventors: Philip E. Eggers, Dublin, Ohio; Anthony J. Manlove, Menlo Park, Calif.

[73] Assignee: Hemostatic Surgery Corporation, Georgetown, Cayman Islands

[21] Appl. No.: 245,308

[22] Filed: May 17, 1994

Related U.S. Application Data

[63] Continuation of Ser. No. 960,475, Oct. 9, 1992, abandoned, which is a continuation-in-part of Ser. No. 877,476, May 1, 1992, abandoned.

[51] Int. Cl.$^6$ .................................................. A61B 17/32
[52] U.S. Cl. ................ 606/29; 606/28; 606/39; 606/46
[58] Field of Search ............... 606/32–34, 28–31, 606/37–42, 45–52; 219/10.75

[56] References Cited

U.S. PATENT DOCUMENTS

| | | |
|---|---|---|
| Re. 33,644 | 7/1991 | Hall .................................. 219/10.75 X |
| 1,975,436 | 10/1934 | Sorrel et al. . |
| 2,181,274 | 11/1939 | Jackson et al. . |
| 2,947,841 | 8/1960 | Pickles et al. . |
| 2,951,927 | 9/1960 | Weller . |
| 3,218,384 | 11/1965 | Shaw . |
| 3,296,364 | 1/1967 | Mason . |
| 3,316,344 | 4/1967 | Kidd et al. . |
| 3,489,884 | 1/1970 | Waseleski, Jr. . |
| 3,515,837 | 6/1970 | Ando . |
| 3,524,966 | 8/1970 | Ando . |
| 3,584,190 | 6/1971 | Marcoux . |
| 3,662,152 | 5/1972 | Weller et al. ................. 219/10.75 X |
| 3,768,482 | 10/1973 | Shaw . |
| 3,826,263 | 7/1974 | Cage et al. . |
| 3,975,819 | 8/1976 | Ando . |
| 3,987,795 | 10/1976 | Morrison . |
| 4,079,192 | 3/1978 | Josse . |
| 4,091,813 | 5/1978 | Shaw et al. . |
| 4,185,632 | 1/1980 | Shaw ................................ 606/45 |
| 4,207,896 | 6/1980 | Shaw . |
| 4,256,945 | 3/1981 | Carter et al. . |
| 4,456,186 | 6/1984 | Ando . |
| 4,481,057 | 11/1984 | Beard . |
| 4,485,810 | 12/1984 | Beard . |
| 4,615,330 | 10/1986 | Nagasaki ......................... 606/46 X |
| 4,622,966 | 11/1986 | Beard ............................... 606/28 |
| 4,626,767 | 12/1986 | Clappier et al. . |

(List continued on next page.)

FOREIGN PATENT DOCUMENTS

| | | |
|---|---|---|
| 0107927 | 5/1984 | European Pat. Off. . |
| 0110692 | 6/1984 | European Pat. Off. . |
| 0130671 | 1/1985 | European Pat. Off. . |
| 0209215 | 1/1987 | European Pat. Off. . |
| 41-2676 | 2/1966 | Japan . |
| 41-1743 | 2/1966 | Japan . |
| 43-18838 | 8/1968 | Japan . |
| 49-5699 | 2/1974 | Japan . |
| 50-84373 | 7/1975 | Japan . |
| 54-57242 | 5/1979 | Japan . |
| 1076772 | 7/1967 | United Kingdom . |

OTHER PUBLICATIONS

Tudbury, C. A., "Skin Effect and Proximity Effect," Sixth Biennial IEEE Conference on Electric Heating, pp. 78–88, Apr. 1963.

Primary Examiner—Stephen C. Pellegrino
Assistant Examiner—Michael Peffley
Attorney, Agent, or Firm—Fish & Neave; Nicola A. Pisano

[57] ABSTRACT

An instrument for use in surgery is provided. The instrument has a heating element with a working surface for providing hemostasis at an auto-regulated temperature. The working surface may include a tapered edge for providing thermally-enhanced cutting and a non-stick coating for operating the instrument at low auto-regulation temperatures. A process for making the instrument is also provided. Additionally, a method of performing surgery on a patient's tissue is also provided.

33 Claims, 9 Drawing Sheets

U.S. PATENT DOCUMENTS

| | | | |
|---|---|---|---|
| 4,640,279 | 2/1987 | Beard . | |
| 4,701,587 | 10/1987 | Carter et al. . | |
| 4,745,264 | 5/1988 | Carter . | |
| 4,770,067 | 9/1988 | Liu et al. . | |
| 4,839,501 | 6/1989 | Cowell . | |
| 4,848,337 | 7/1989 | Shaw | 606/45 |
| 4,869,248 | 9/1989 | Narula | 606/45 |
| 4,936,842 | 6/1990 | D'Amelio et al. . | |
| 5,013,312 | 5/1991 | Parins | 606/37 |
| 5,047,025 | 9/1991 | Taylor et al. . | |
| 5,071,419 | 12/1991 | Rydell et al. . | |
| 5,078,256 | 1/1992 | Taylor et al. . | |
| 5,080,660 | 1/1992 | Buelna . | |
| 5,223,689 | 6/1993 | Cowell et al. | 219/10.75 X |

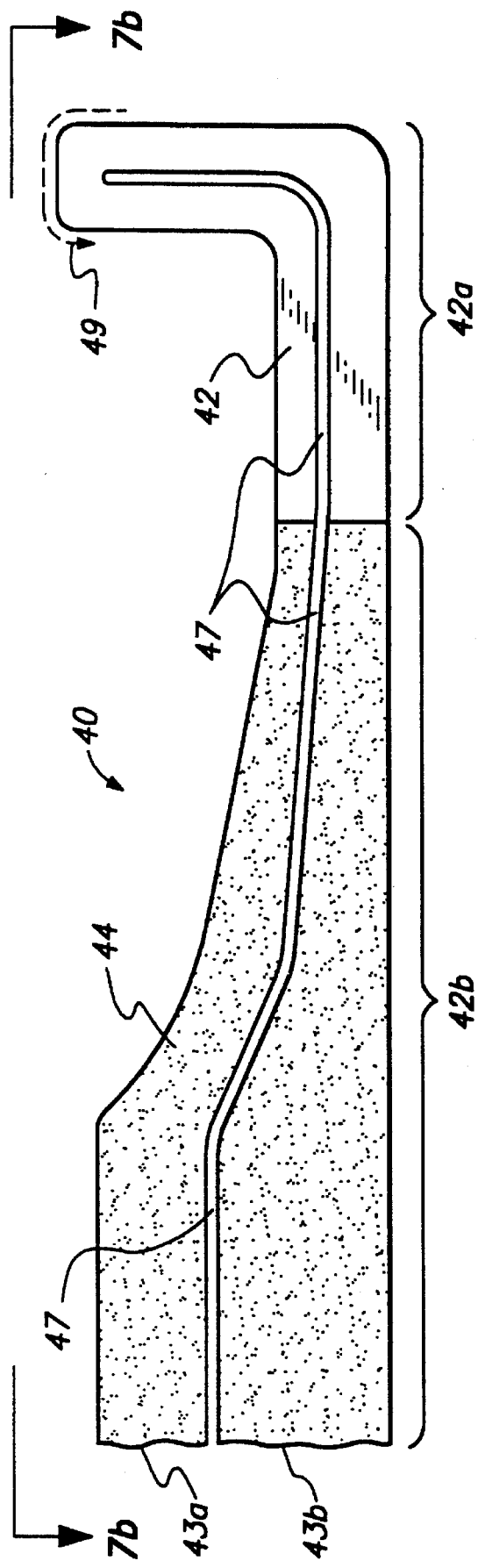
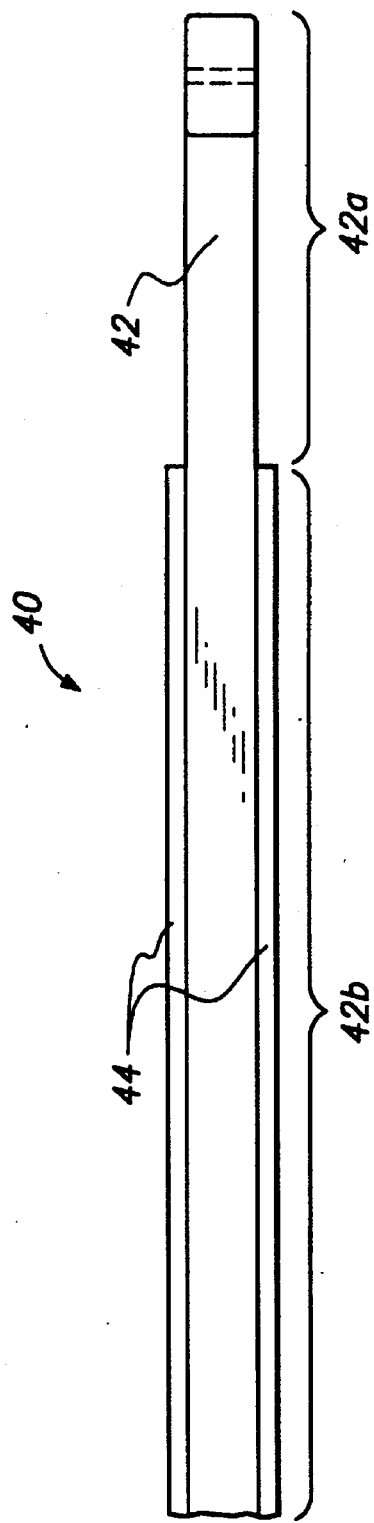
FIG 7a
FIG. 7b

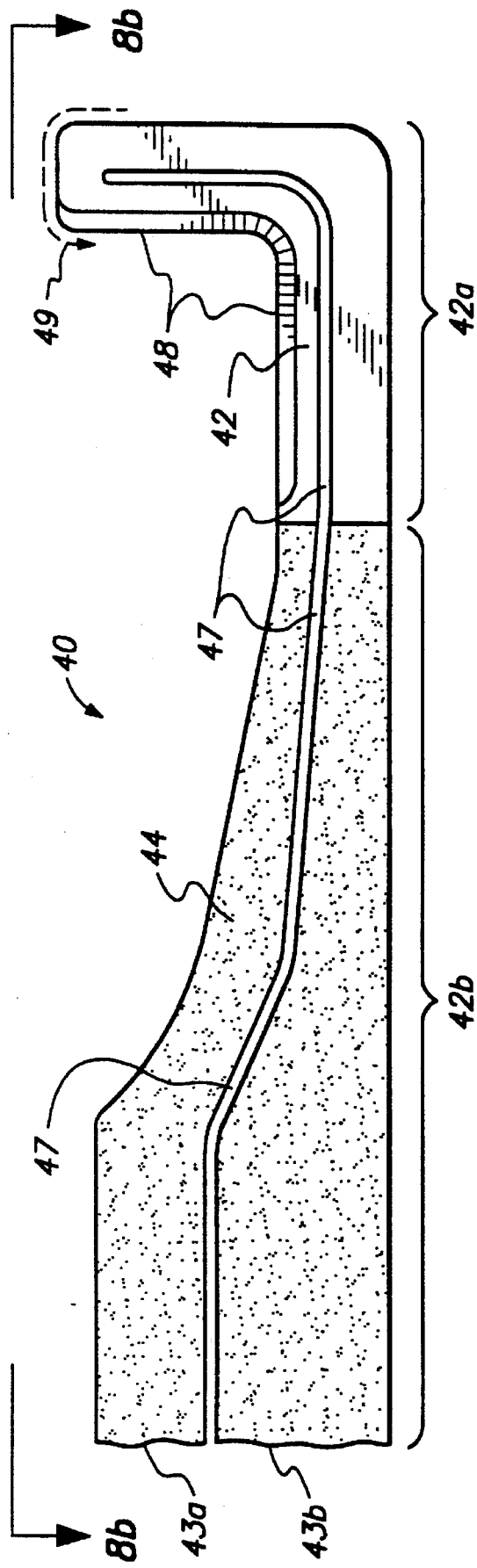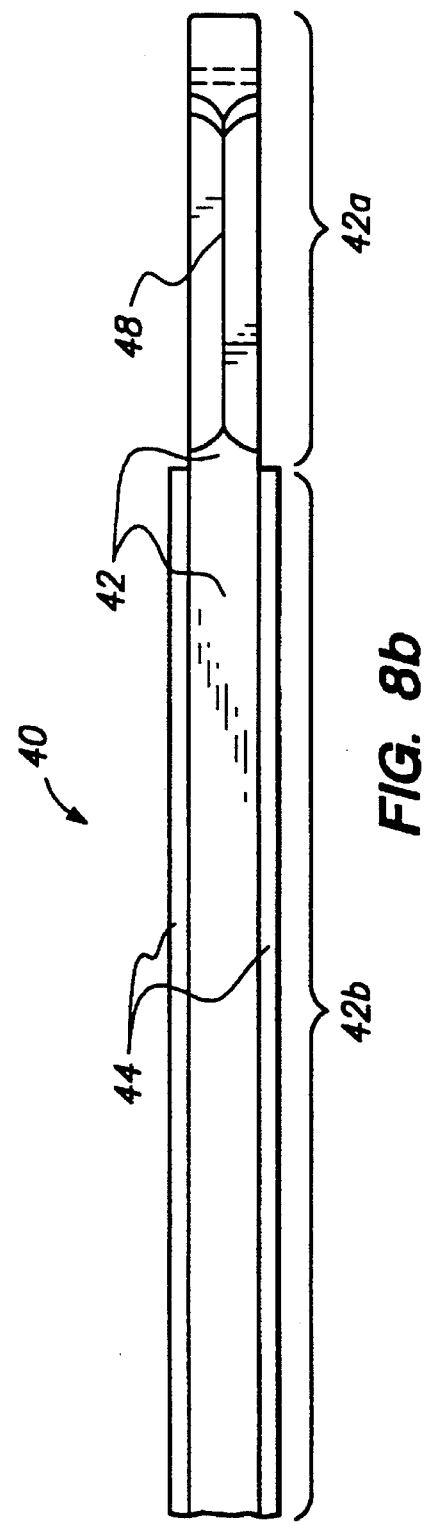
FIG 8a
FIG. 8b

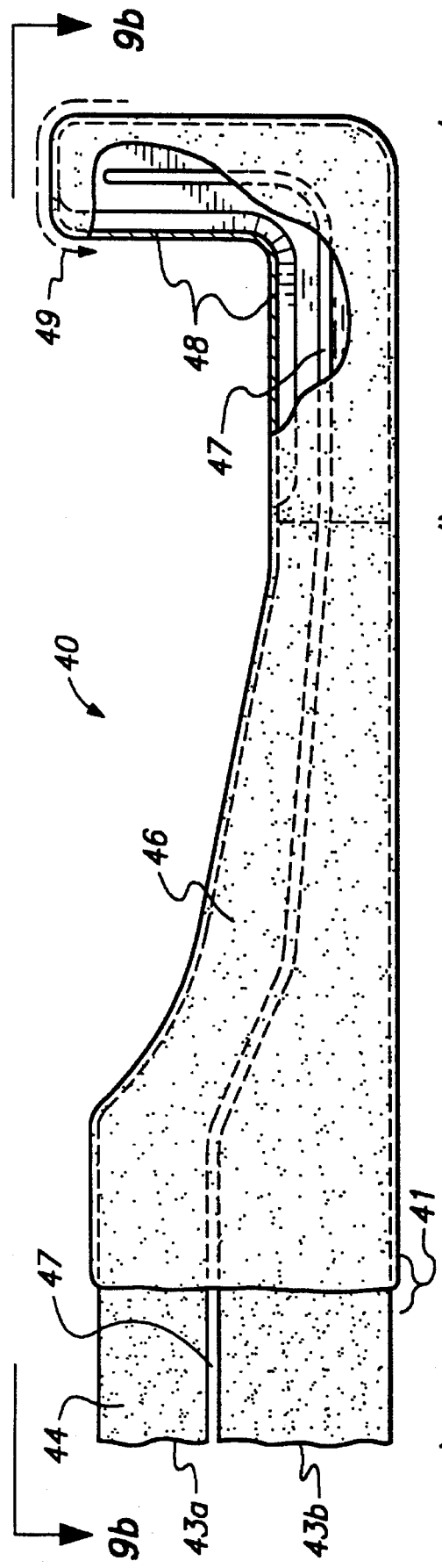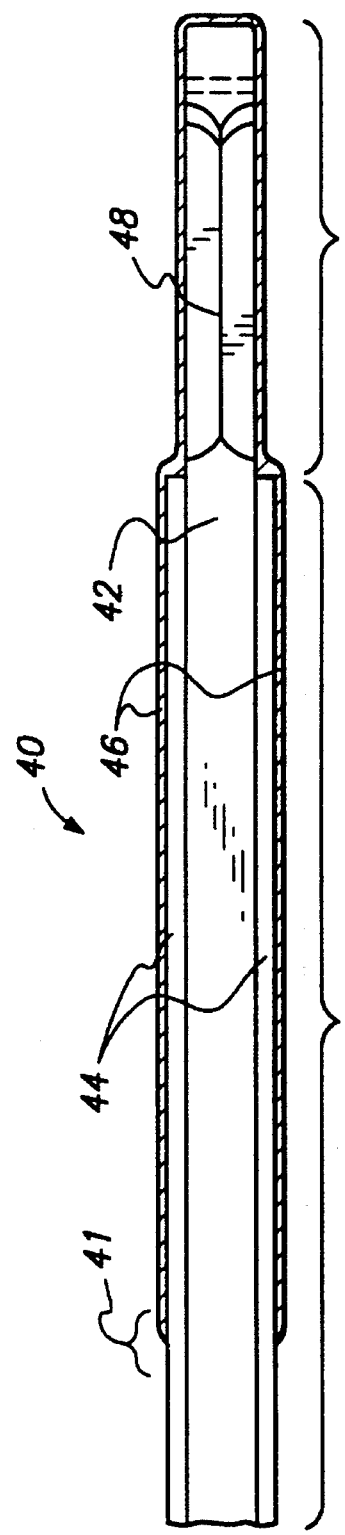
FIG 9a
FIG. 9b

SURGICAL INSTRUMENT WITH AUTO-REGULATING HEATER AND METHOD OF USING SAME

CROSS REFERENCE TO RELATED APPLICATION

This is a continuation of application Ser. No. 07/960,475, filed Oct. 9, 1991 now abandoned, entitled SURGICAL INSTRUMENT WITH AUTO-REGULATING HEATER AND METHOD OF USING SAME, which is a continuation-in-part of application Ser. No. 07/877,476, filed May 1, 1992 now abandoned.

BACKGROUND OF THE INVENTION

This invention relates to instruments for use in surgery. More particularly, this invention relates to surgical instruments with an auto-regulating heater.

It is known to provide surgical scalpels which employ a blade with an adjacent resistive heating element. The resistive heating element provides thermally-enhanced cutting, in addition to hemostasis, when electrical current is passed through the element. Although such resistive heating elements can be readily brought to a suitably high and constant temperature in air prior to contacting tissue, they rapidly cool when brought into contact with tissue. During surgery, non-predictable and continually varying portions of the blade contact the tissue as it is being cut. As the blade cools, its ability to cut tissue and provide hemostasis becomes markedly less effective. Furthermore, tissue tends to adhere to the blade. If additional power is applied by conventional means to counteract this cooling, the additional power may be delivered to the uncooled portions of the blade, thus resulting in tissue damage and blade deterioration.

Shaw U.S. Pat. No. 4,185,632 shows an improved surgical cutting instrument in which the temperature of the cutting portion of the blade is self-regulating. Radio frequency electrical currents maintain the temperature within an elevated preselected temperature range. These currents flow within variable skin depths in an electrical conductor disposed near the cutting edge of the blade. This variable skin depth effect produces self-regulation of the blade temperature.

Although the cutting instrument shown in the above-referenced Shaw U.S. Pat. No. 4,185,632 has improved temperature regulation over other surgical scalpels, further improvements are possible. For example, such instruments may be designed to provide low cost and simplicity of manufacturing.

Additionally, reducing the adherence of tissue to a surgical instrument is also desirable. Coagulum buildup and sticking limits the usefulness of an instrument and may cause undesirable tissue damage and bleeding. Also, the adherence of tissue to surgical instruments limits the surgeon's control of the instrument.

In light of the above, it would therefore be desirable to provide a low cost, easy to manufacture, surgical instrument with an auto-regulating heater for providing temperature regulation.

It would still further be desirable to provide a surgical instrument which reduces the adherence of tissue and coagulum to the instrument.

SUMMARY OF THE INVENTION

In view of the foregoing, it is an object of this invention to provide a low cost, easy to manufacture, surgical instrument with an auto-regulating heating element for providing temperature regulation.

It is a still further object of this invention to provide a surgical instrument which reduces the adherence of tissue and coagulum to the instrument.

In accordance with the present invention there is provided an instrument for use in surgery comprising: a shaft having a proximal end and a distal end; a heating element disposed from the distal end of the shaft and having a working surface for contacting tissue, wherein the working surface is maintained at an auto-regulated temperature, the heating element comprising a material having a skin depth responsive to the temperature of the heating element and that decreases as the temperature of the element falls below the auto-regulated temperature; first and second electrodes disposed from the proximal end of the shaft; and means connecting the first and second electrodes to the heating element.

The working surface of the instrument may also include an optional tapered edge for thermally-enhanced cutting of tissue and an electrically insulating non-stick coating to reduce coagulum buildup. Furthermore, the instrument may include a heater support member, interposed between the distal end of the shaft and the heating element, for reducing conduction of heat from the heating element to the shaft.

In an alternative embodiment of the present invention, the heating element includes: a metal substrate having both a high-temperature working surface region for contacting tissue and a low-temperature region for disposing the heating element adjacent a distal end of a shaft, the high-temperature working surface region maintained at an auto-regulated temperature, the metal substrate comprising a material having a skin depth responsive to the temperature of the high-temperature working surface region and that decreases as the temperature of the high-temperature working surface region falls below the auto-regulated temperature. A layer of metal having a low thermal conductance is overlaid on the low-temperature region of the metal substrate to reduce the conductance of heat from the high-temperature working surface region to the low-temperature region of the metal substrate.

The working surface of the alternative embodiment of the heating element may also include an optional tapered edge for thermally-enhanced cutting of tissue. Furthermore, the heating element may also include an electrically-insulating non-stick coating to reduce coagulum buildup.

The present invention also includes a process for making a heating element for use in surgery. This process includes the steps of: forming a substrate with both a high-temperature working surface region for contacting tissue, and a low-temperature region for disposing the heating element adjacent a distal end of a shaft, the high-temperature working surface region to be maintained at an auto-regulated temperature, the substrate comprising a material having a skin depth responsive to the temperature of the high-temperature working surface region and that decreases as the temperature of the high-temperature working surface region falls below the auto-regulated temperature; and providing a metal overlayer on the low-temperature region of the metal substrate, the overlayer having a low thermal conductance for reducing the conductance of heat from the high-temperature working surface region to the low-temperature region of the metal substrate. This process may also include the step of providing a tapered edge on the working surface for thermally-enhanced cutting of tissue. Furthermore, the process may also include the step of providing a coating of an electrically-insulating non-stick material on the working surface.

In addition to providing an instrument for use in surgery and providing a process for making such instruments, the present invention also includes a method of performing surgery on a patient's tissue. This method uses a shaft and a heating element disposed from the handle, the heating element having a working surface for contacting tissue, maintained at an auto-regulated temperature, the heating element comprising a material having a skin depth responsive to the temperature. The method comprising the steps of, (a) connecting the instrument to a power source for supplying alternating current ("AC") electrical power to the heating element;

(b) disposing the working surface of the instrument adjacent to the tissue;

(c) selecting and controllably supplying a current from the power source to the heating element to maintain the working surface substantially at the auto-regulated temperature; and (d) placing the working surface in substantial contact with the patient's tissue so as to transfer heat from the working surface to the patient's tissue.

Further steps of the method include supplying a substantially constant current from the power source so as to maintain the heating element at an auto-regulated temperature in the range of approximately 100° to 600° C.

BRIEF DESCRIPTION OF THE DRAWINGS

The above and other objects and advantages of the present invention will be apparent upon consideration of the following detailed description, taken in conjunction with accompanying drawings, in which like reference characters refer to like parts throughout, and in which:

FIGS. 7A and 7B are, respectively, plan and elevation views of an alternative embodiment of the present invention incorporating a monolithic heating element;

FIGS. 8A and 8B are, respectively, plan and elevation views of a surgical instrument constructed as shown in of FIGS. 7A and 7B, further incorporating the optional tapered thermally-enhanced cutting edge of the present invention; and FIGS. 9A and 9B are, respectively, plan and elevation views of a surgical instrument similar to that of FIGS. 8A and 8B, further incorporating the optional non-stick coating of the present invention.

DETAILED DESCRIPTION OF THE INVENTION

Figure 1:
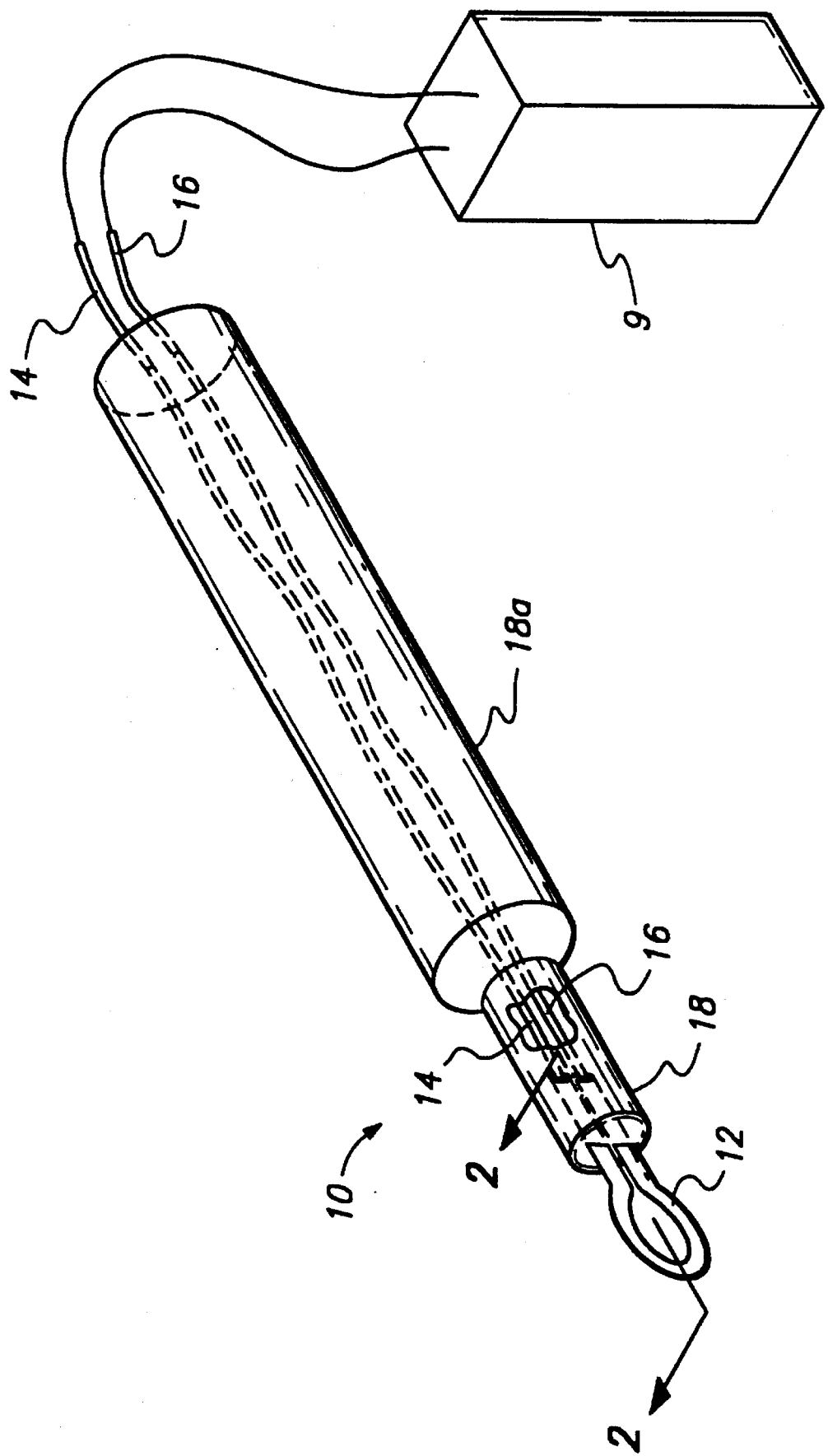
FIG. 1 is a perspective view, partly in section, of surgical apparatus constructed in accordance with the principles of the present invention.
Figure 2:
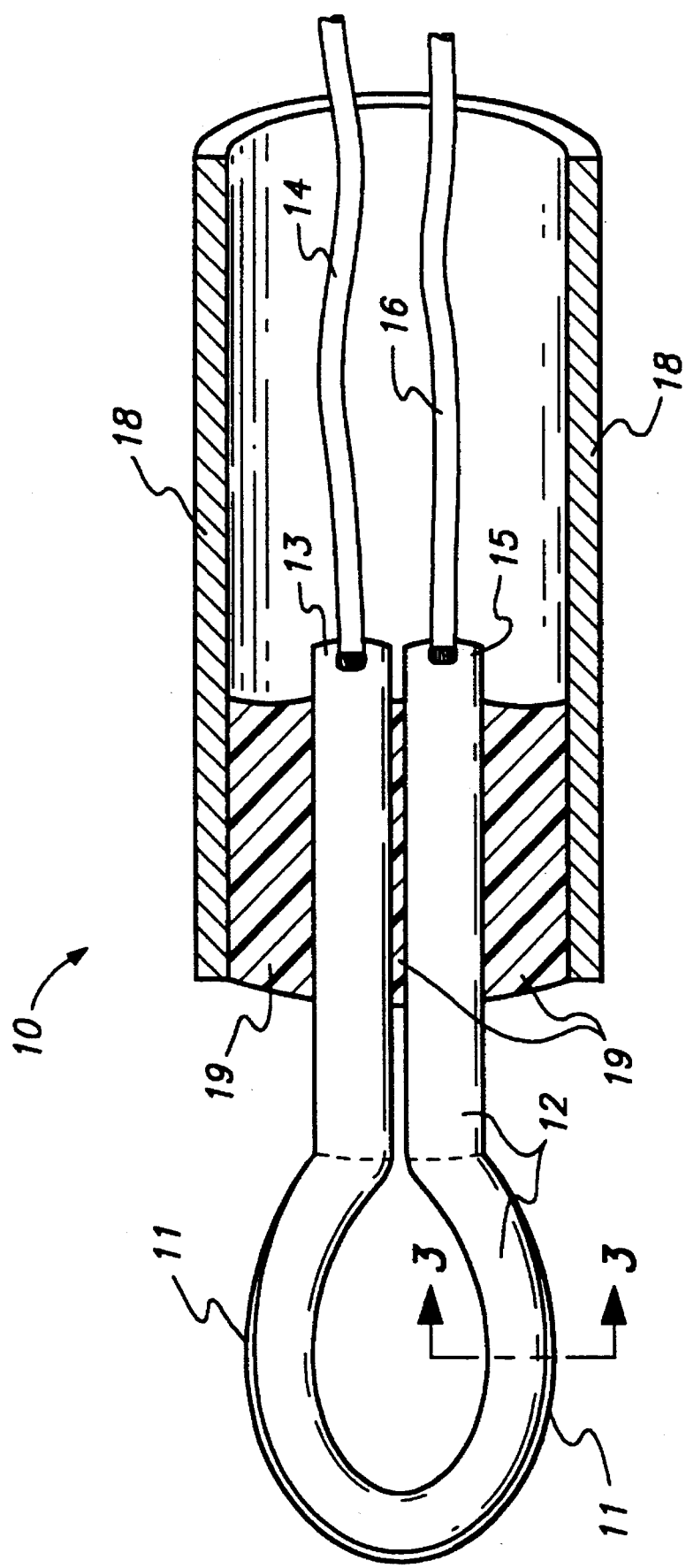
FIG. 2 is a cross-sectional view of the surgical instrument of FIG. 1, taken along line 2—2 of FIG. 1.

Referring to FIGS. 1 and 2, an illustrative embodiment of surgical instrument 10 of the present invention is described. The working surface of this instrument may be used for causing hemostasis of incised tissue or for directly coagulating small tissue masses, either with or without simultaneously incising the tissue. Surgical instrument 10 includes a shaft 18 having proximal and distal ends. Shaft 18 may be either flexible or rigid, depending upon the intended application. A working end comprising heating element 12 is disposed from the distal end of shaft 18, while handle 18A for facilitating manipulation of the instrument is disposed from the proximal end of shaft 18. Electrical leads 14 and 16 extend both to the handle, where they are then connected to power source 9, and to heating element 12 on the distal end of shaft 18.

A unique feature of the present invention is that heating element 12, in addition to providing the source of thermal energy for the surgical instrument, serves as the working surface of the instrument. This feature of the present invention eliminates the need for providing an additional metal (e.g., a cutting edge) that the heating element is disposed adjacent to, and thus, reduces the cost and simplifies the manufacturing of the instrument. More importantly, the energy generated in the heating element is directly manifested by the working surface temperature, with no temperature gradients resulting from conduction of heat from a higher temperature heat generation region to the working surface.

Surgical instrument 10 works as follows. Power source 9 provides an alternating current (AC) electrical potential to terminals 13 and 15, respectively, of heating element 12 through electrical leads 14 and 16. In response to the imposed electrical potential, an electrical current is conducted through heating element 12. That current results in joulean heating, which raises the temperature of heating element 12 above body temperature (i.e., approximately 37° C.) to facilitate hemostasis and optionally permit thermally-enhanced cutting of tissue.

The present invention provides auto-regulation of the temperature of heating element 12. This self-regulating temperature feature results from constructing heating element 12 of a ferromagnetic material, or other material which undergoes a similar transition in current conduction properties when the temperature of the material varies. It is known that in such materials an AC current is confined to a region adjacent the surface of the material. This phenomena is commonly called the "skin effect." The current density is generally greatest at the surface and decreases in magnitude further into the material where the electric field approaches zero. The depth at which the skin effect current is reduced to about 37 percent of its surface value is referred to as the "skin depth" and is a function of the electrical resistivity, the magnetic permeability of the material conducting the current, and the frequency of the applied alternating electric potential. It is known that the skin depth $T_{SD}$, in centimeters, can be generally represented by the equation:

$$T_{SD} = (5 \times 10^3) \mathrm{sqrt}(rho/[uf])$$

where rho is electrical resistivity in ohm-centimeters, u is relative magnetic permeability, and f is frequency in Hertz.

Ferromagnetic materials such as iron, nickel, cobalt, and their alloys, exhibit large changes in relative permeability as the temperature goes through a transition point called the "Curie" point. Because the relative permeability changes in response to the temperature of the material, the associated skin depth also changes, and therefore the amount of current conduction through the skin layer undergoes a transition near the Curie point. This transition in current conduction properties is used, as described hereinafter, to achieve auto-regulation of the temperature of heating element 12.

An auto-regulated surgical instrument is obtained in accordance with the present invention by causing a radio frequency (RF) current to flow in heating element 12. Heating element 12 may be composed of a ferromagnetic material or the like and uses the skin effect of the material to auto-regulate the temperature of the heating element. Heating element 12 is constructed of a material having a current conduction transition at or near the auto-regulation temperature desired for the particular surgical application. When heating element 12 is heated so that when a working surface of heating element 12 contacts tissue, that region of the heating element cools below the transition temperature. In response to the local temperature drop in the heating element, the associated skin depth responsively decreases as a result of the Curie transition in the heating element material. The reduced skin depth in turn results in an increase in local power dissipation, so that the temperature automatically tends to increase towards the auto-regulation temperature. Accordingly, the present invention uses the skin depth effect of the heating element material to maintain the working surface of the surgical instrument substantially at the auto-regulated temperature throughout the range of conditions encountered during surgery.

For example, for many iron-nickel alloys the Curie transition occurs at about 450° C., above which the relative permeability is near unity. Below about 450° C., the relative permeability is high, perhaps 100 to 1000, for the magnetic field strengths suitable for use in surgical instruments. Thus, when the local temperature of a heating element constructed of this material falls below about 450° C., due to local cooling of the heating element when it comes into contact with cool tissue, the associated skin depth decreases more than 10 to 1. The decrease in skin depth results in an increase in local power dissipation and, thus, an increase in heating to provide auto-regulation of the heating element temperature.

In accordance with the present invention, heating element 12 may be composed of a ferromagnetic material or other material which undergoes a similar transition in current conduction properties, as the temperature of the material varies through the desired auto-regulation temperature, as discussed above. Preferably, heating element 12 is composed of an alloy of nickel and iron. Examples I and II, provide illustrative embodiments wherein the auto-regulation temperature is varied by varying the percentage of nickel and iron present in heating element 12.

EXAMPLE I

For an auto-regulation temperature of approximately 315° C. at 1.8 megahertz, the alloy may be approximately 42% nickel and 58% iron. Such an alloy is available as LOW EXPANSION ALLOY 42, from Carpenter Technology Corporation of Reading, Pa. and has the following characteristics: unannealed, a hardness of approximately 91 Rockwell B, a tensile strength of approximately 98.5 ksi, an electrical resistivity at 23° C. of approximately 373 Ohms-cir mil/foot and a coefficient of thermal expansion of approximately 3.1 (IN/IN F×10–6) from approximately 77° to 700° F. Applicants believe that satisfactory auto-regulation performance can be obtained with devices constructed of this alloy wherein the working end of the heating element is approximately 18 mils (0.46 mm) thick and has a thermostat cold finish.

EXAMPLE II

For an auto-regulation temperature of approximately 550° C. at 1.8 megahertz, the alloy may be approximately 51% nickel and 49% iron. Such an alloy is available as GLASS SEAL 52, also from Carpenter Technology Corporation of Reading, Pa., and has the following characteristics: unannealed, and with a coefficient of thermal expansion of approximately 10.0 (IN/IN C×10–6) from approximately 25° to 550° C. Applicants believe that satisfactory performance can be obtained with devices constructed of this alloy wherein the working end of the heating element is approximately 20 mils (0.51 mm) thick.

After the heating element material has been selected, whether or not containing nickel or iron as in Examples I and II above, the heating element may then be configured into a variety of shapes, only one of which is shown in FIGS. 1 and 2. Of course, the particular shape desired depends upon the application of the particular surgical instrument.

In accordance with another feature of the present invention, it is desirable that the cross-sectional dimensions of heating element 12 be chosen to allow the electrical conductance of heating element 12 to change by at least a factor of 4 to 5 as the temperature of the working surface varies near the auto-regulation temperature. This feature of the present invention is illustrated by FIGS. 3A and 3B.

Figure 3A:
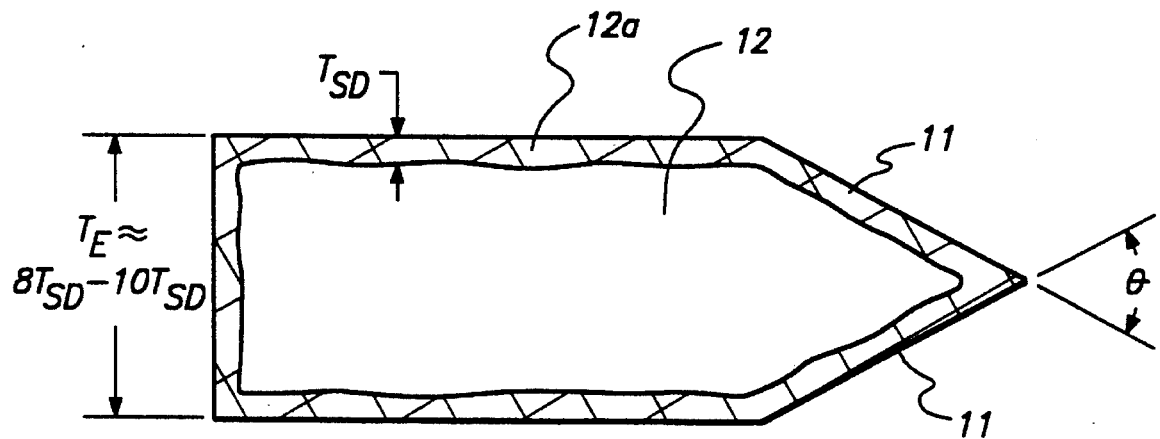
FIGS. 3A and 3B are illustrative cross-sectional views of heating element 12 of FIGS. 1 and 2, taken along line 3—3 of FIG. 2, at temperatures slightly below and above the auto-regulation temperature, respectively.
Figure 3B:
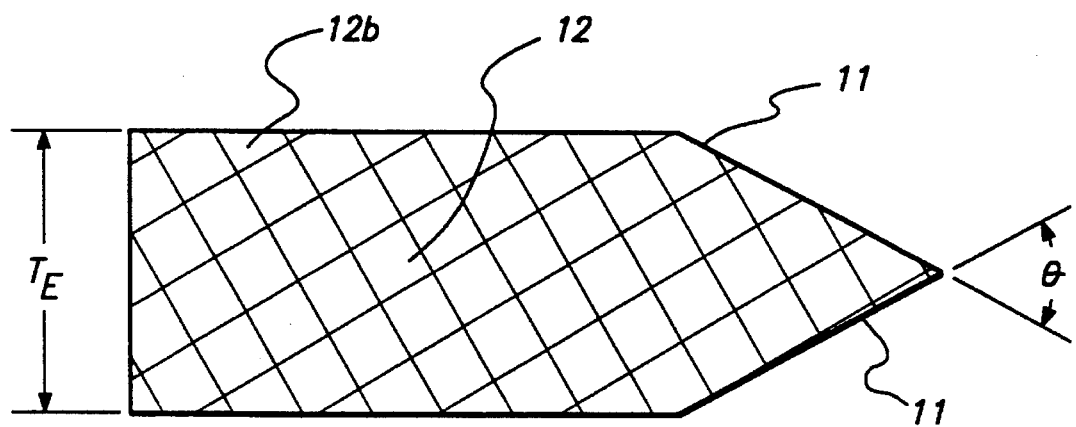

As shown in FIG. 3A, when the working surface temperature is slightly below the auto-regulation temperature, current 12a is confined to conduct in a region defined by the skin depth $T_{SD}$ of heating element 12. In accordance with the present invention, it is desirable that thickness $T_E$ of heating element 12 be approximately eight to ten times the skin depth $T_{SD}$, so that as the temperature of heating element 12 varies near the auto-regulation temperature, the electrical conductance of the element changes by a factor of about four to five. In FIG. 3B, where the heating element is at a working surface temperature slightly in excess of the auto-regulation temperature, electrical current 12b conducts throughout substantially the entire cross section of heating element 12 because the skin depth is then greater than half of the thickness $T_E$ of heating element 12. Thus, the effective electrical conductance of heating element 12 increases by a factor of four to five as it varies near the autoregulation temperature, as shown in FIGS. 3A and 3B.

After the shape and cross-sectional dimensions of heating element 12 are chosen, heating element 12 may be constructed using any method which produces geometrical dimensions that are consistent with the desired design tolerances of the working surface. For example, such methods include electric-discharge machining (EDM), blanking and chemical milling.

Heating element 12 is affixed to the distal end of shaft 18 by potting material 19, which electrically isolates heating element 12 and electrical leads 14 and 16 from shaft 18. Potting material 19 should, in addition, be suitable for use in the temperature range experienced by heating element 12. Furthermore, it is desirable that potting material 19 be able to withstand typical conditions encountered in steam-sterilization procedures and have a viscosity that would allow it to be placed into the inner portion of shaft 18. Accordingly, the potting material may be comprised of plastic, ceramic, silicone or epoxy-based materials.

Preferably, shaft 18 is made of a high thermal conductivity material so as to dissipate (i.e., distribute over the full length of said shaft) that heat which conducts from heating element 12 located at the distal end of the shaft. This feature reduces the potential that non-targeted tissue will be subjected to high temperatures that might cause damage.

For example, shaft 18 may be constructed of copper or the like and be plated with chrome on its outer surface. The chrome plating provides a cosmetic dull-mat finish to the copper, which would normally otherwise oxidize, and facilitates conventional steam-sterilization procedures.

Electrical leads 14 and 16, which are connected to power source 9, should be capable of delivering the necessary AC current to heating element 12 with low electrical power loss. To avoid behavior associated with the skin effect, electrical leads 14 and 16 may each be composed of multiple strands of wire, wherein the individual strands are insulated from each other. The insulation allows AC current to flow through each individual strand but not between strands. A suitable wire is available as TYPE 2 LITZ WIRE (5×16×40), from Cooner Wire of Chatsworth, Calif. This particular wire is composed of 5 groups of 16 strands (i.e., a total of 80 strands), wherein each strand, which are insulated from each other, is of type 40 AWG.

In accordance with another feature of the present invention, when it is desired to operate the surgical instrument below the temperature range of 450°–500° C., heating element 12 may also be coated with an electrically-insulating "non-stick" coating. Such a coating reduces the accumulation of coagulum on the working surfaces of heating element 12 when operated at low temperatures. The application of such coatings to surgical instruments, including a description of preferred coatings for the present invention, are discussed in Shaw et al. U.S. Pat. No. 4,848,337, which is hereby incorporated by reference in it's entirety. This patent describes an adherent coating for reducing the adherence of tissue to a surgical instrument for incising and causing hemostasis. Such coating includes materials selected from the group consisting of silicones, polydimethyisiloxanes, fluoride-metal composites and fluorocarbon polymers.

If a non-stick coating is desired, the coating may, more preferably, be either a fluorine-containing mixture, such as polytetrafluoroethylene (PTFE), or a fluorotelomer-based mixture. In particular, the coating may be either of type XYLAN® 8110/870 Black, available from Whitford Corporation of West Chester Pa., which is PTFE-based, or type VYDAX® 1000 FLUOROTELEMER DISPERSION, available from E. I. du Pont de Nemours & Co., Inc., of Wilmington, Del., which is a fluorotelomer based-mixture. VYDAX® is preferred for longer-lasting applications where the surgical instrument will be reused multiple times. Furthermore, the VYDAX® thickness should preferably be in the range of approximately 0.3 to 0.4 mil (0.0075 to 0.01 mm).

An important consideration for surgical "cutting" instruments is to reduce the exposure of non-operative tissue to surgically sharp edges. During manipulation of surgical instruments, inadvertent contacting of tissue might result in unwanted cutting (and associated bleeding). Hence, the surgical "cutting" instrument constructed in accordance with the present invention is "sharp" only when the cutting instrument is activated.

In accordance with the present invention, heating element 12 of FIGS. 1 and 2 may include a tapered edge 11 that is atraumatic, i.e., not surgically sharp, at body temperature, but is able to cut tissue when heating element 12 is energized. A cross-sectional view of tapered edge 11 is shown in FIGS. 3A and 3B. This "thermally activated cutting" edge is accomplished by having heating element 12 heat the issue to weaken its structure. The weakened tissue may then be severed by a relatively blunt instrument compared to the mechanically sharp surgical edge required to sever tissue at body temperature. The preferred cutting edge of the present invention has a taper angle, theta, at the apex of heating element 12, in the range of approximately 15° to 50°, and more preferably, 20° to 40°. The cutting edge comprises material having hardness, as measured by the Rockwell Hardness Method, of less than about 40 Rockwell C. Such an edge, when heated to temperatures in excess of approximately 260° C., produces a precise incision through tissue, but is not hard enough to be ground with an edge sufficiently sharp to cut tissue at body temperature. Furthermore, instruments constructed in accordance with this feature of the present invention may be conveniently bent and configured during surgery, by the surgeon, to reach tissue regions not otherwise accessible.

Figure 4:
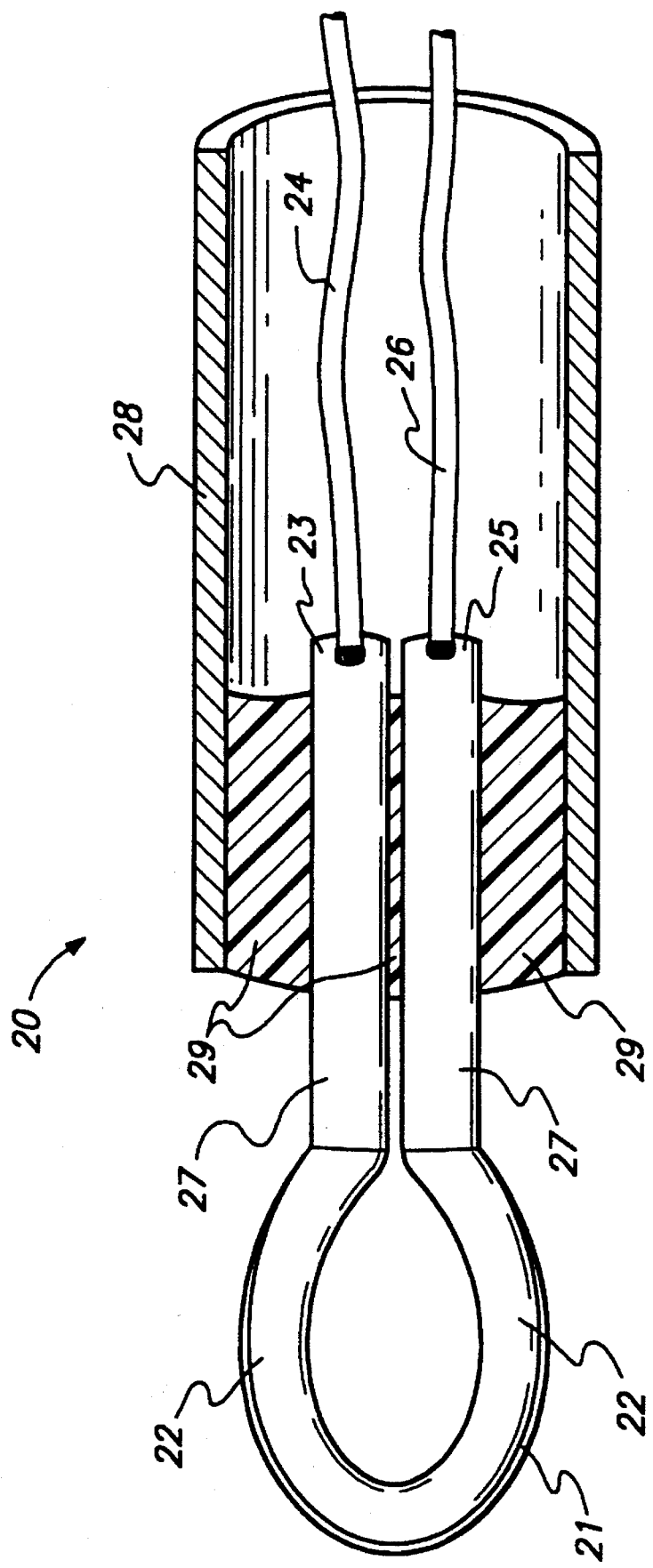
FIG. 4 is a cross-sectional view similar to FIG. 3, of an alternative dual-metal embodiment of the surgical instrument of the present invention.

Referring now to FIG. 4, an alternative embodiment 20 of the present invention is described. Surgical instrument 20 is similar in other respects to surgical instrument 10 shown in FIGS. 1–3, except for the addition of heater support member 27 interposed between heating element 22 and shaft 28. Thus, surgical instrument 20 includes shaft 28, electric leads 24 and 26, terminals 23 and 25, and potting material 29. The instrument may also include a tapered edge 21 for providing thermally-enhanced cutting.

Heater support member 27 is composed of a low thermal conductance material for limiting heat conduction from heater element 22 to the shaft. Heater support member 27 reduces heating of the distal portion of shaft 18, and thereby reduces the likelihood of heating tissue remote from the surgical site.

In accordance with the present invention, heater support member 27 furthermore does not itself generate heat due to the AC current that passes through it. As discussed above, it is desirable to confine and localize the high temperatures present in heating element 22 so as to not inadvertently damage or heat non-operative tissue. Thus, it is desirable to be able to maintain heater support member 27 and shaft 28 at temperatures below approximately 60°–70° C. even when heater element 22 is at maximum operating temperature. Heater support member 27 has low thermal conductance and does not dissipate significant electrical power as current is conducted through it (i.e., has low electrical resistance). Thus, under these conditions, heater support member 27 stays at relatively low temperatures, compared to those experienced by heating element 22.

A preferred material for heater support member 27 comprises a low thermal conductivity nonferromagnetic metal or alloy such as stainless steel, for example, TYPE 304 stainless steel. The use of nonferromagetic alloys or metals in heater support member 27 allows the AC current passing to be conducted throughout substantially the entire cross section of the heater support.

Heater support member 27 may be connected to heater element 22 by any method that results in a low electrical resistivity junction. Such methods include thermally inert gas welding (TIG) and, more preferably, electron beam welding or laser-assisted welding.

Figure 5:
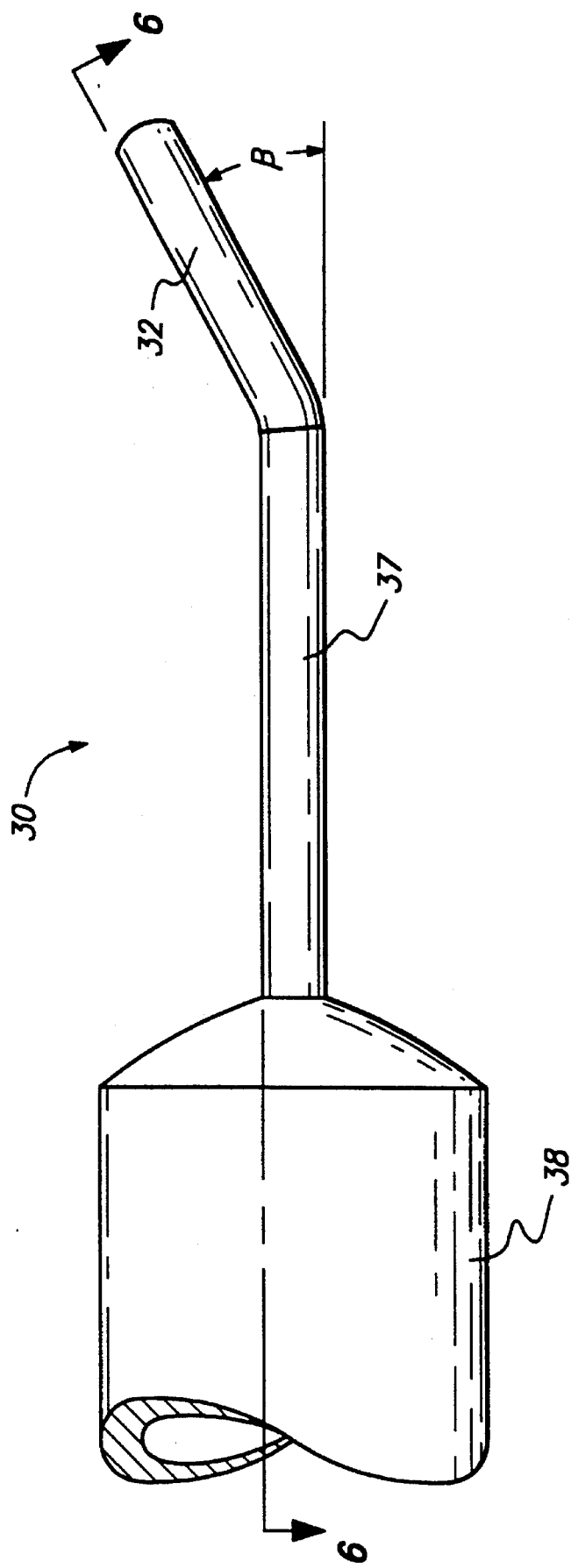
FIG. 5 is a side view a dual-metal surgical instrument of the present invention incorporating a serpentine-shaped heating element.
Figure 6:
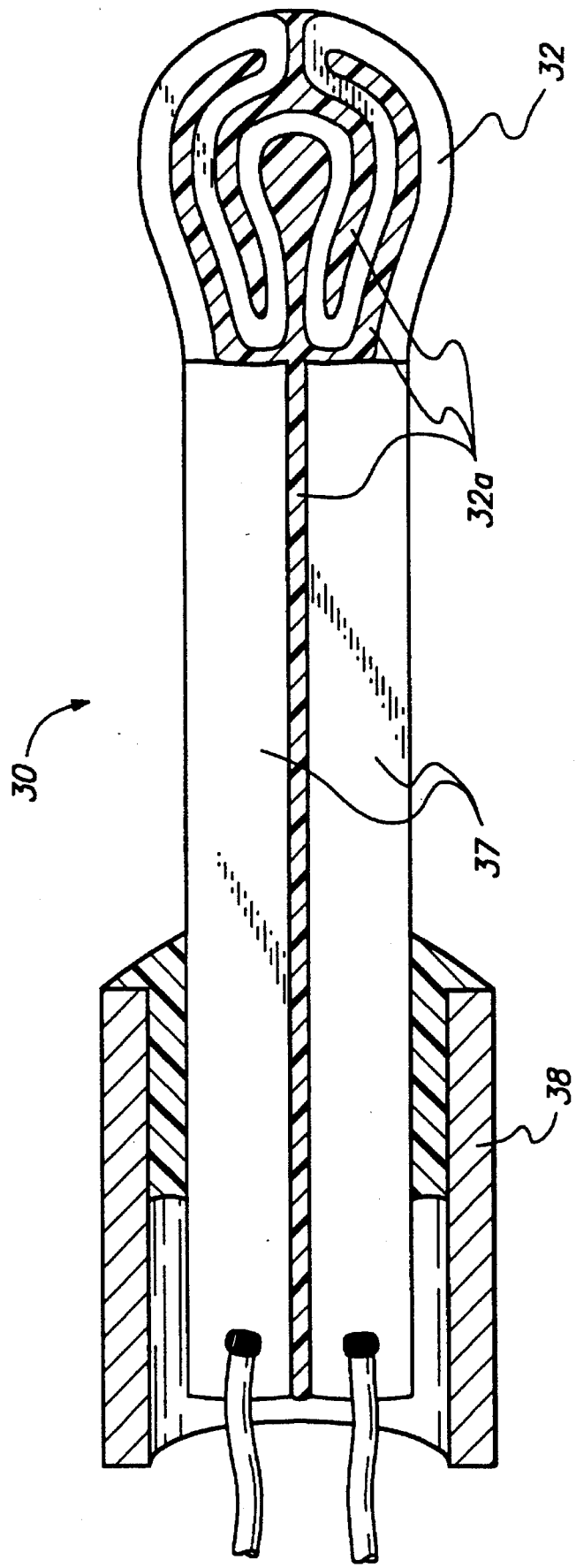
FIG. 6 is a plan view, partly in section, of the surgical instrument of FIG. 5, taken along line 6—6 of FIG. 5.

FIGS. 5 and 6 show a "serpentine" embodiment 30 of a heating element constructed in accordance with the present invention, wherein the "serpentine" heating element 32 is disposed at an angle beta to the longitudinal axis of shaft 38. Angle beta is selected depending upon the type of surgical procedure to be employed, and may be, for example, 30 degrees. Heating element 32 is attached to shaft 38 via low thermal conductance heater support member 37 that confines the heat generated in heating element 32 to the working surface. This embodiment provides an increased working surface area in comparison to the heating elements of FIGS. 1–4, as may be desirable for some surgical procedures. "Serpentine" heating element 32 may also include alumina cement 32a, or other similar material, to fill the air gaps between the scrolls of the heating element to provide a smooth, easy-to-clean surface.

As described hereinabove, the embodiments of the present invention of FIGS. 4–6, include a "heater support member" interposed between the heating element and the distal end of the shaft. As discussed above, the heater support member reduces the leakage of heat from the heater element to the instrument shaft and is therefore fabricated from a material having a lower thermal conductivity than the material comprising the heating element. Thus, the embodiments of FIGS. 4 to 6 may be referred to as "dual-metal" embodiments.

Referring now to FIGS. 7–9, preferred embodiments of monolithic heating elements of the present invention are described. Heating element 40 of FIGS. 7A and 7B, includes auto-regulating metal substrate 42, overlayer 44, optional taper 48 (see FIGS. 8A and 8B) and optional non-stick coating 46 (see FIGS. 9A and 9B).

Auto-regulating metal substrate 42 comprises a ferromagnetic material, or other material which undergoes a similar transition in current conduction properties, when the temperature of the material varies. Suitable materials for use in heating element 40 are described hereinbefore with respect to the embodiments shown in FIGS. 1–6.

Auto-regulating metal substrate 42 has a high-temperature working surface region 42a and a low-temperature region 42b. An AC electric potential placed across terminals 43a and 43b in low-temperature region 42b causes an AC electric current to flow between terminals 43a and 43b and thus, through high-temperature working surface region 42a. Terminals 43a and 43b are separated by an isolation air gap 47, which electrically isolates terminal 43a from 43b, and which forces the AC current flowing through heating element 40 to conduct around loop 49 in high-temperature working surface region 42a. Isolation air gap 47, as was the case with the "serpentine" heating element shown in FIG. 6, may also be filled with alumina cement or other similar material to provide a smooth easy-to-clean surface. In accordance with the present invention, the AC current is conducted within the skin-depth of substrate 42 in high-temperature working surface region 42a and around loop 49. The resulting power dissipation heats region 42b to high temperatures sufficient to cause hemostasis of tissue and, if desired, thermally-enhanced cutting of the tissue (FIGS. 8A and 8B). Auto-regulation of the temperature of high-temperature working surface region 42a is achieved by constructing region 42a of auto-regulating metal, such as a ferromagnetic metal or the like, as discussed above with respect to the embodiments of the surgical instrument shown in FIGS. 1–6.

As for the previously-described embodiments, auto-regulating metal substrate 42 may be configured in a variety of shapes, depending upon the application of the particular surgical instrument. As described hereinbefore, substrate 42 may be constructed using a variety of methods and may include a thermally-enhanced cutting edge (FIGS. 8A and 8B).

Low-temperature region 42b of substrate 42 is covered with overlayer 44, a material that confines the heat generated in high-temperature working surface region 42a to the working surface area of the surgical instrument. Overlayer 44 may comprise a nonferromagnetic metal or alloy having a low thermal conductance and thus serves the same purpose as the heater support member discussed above with respect to dual-metal embodiments shown in FIGS. 4–6. However, in contrast to the embodiments of FIGS. 4–6, the low thermal conductance region is not separately welded or otherwise connected to the heating element 40. Thus, the embodiment of FIG. 7 comprises a monolithic heating element.

To reduce resistive heating of overlayer 44 caused by the AC current passing therethrough, the material comprising the overlayer should have a low electrical resistance in addition to low thermal conductance. Because of this preference for both low thermal conductance and low electrical resistance of overlayer 44, the selection of suitable materials for the overlayer may involve trade-offs with respect to the thickness, length and composition of the overlayer.

For example, since different metals and alloys have different values for both thermal conductivity and electrical resistivity, one metal may give low electrical resistance, but have high thermal conductance. Thermal conductance is proportional to the geometrical area and inversely proportional to the length of the thermal conductor, while electrical resistance has an opposite behavior (i.e., electrical resistance is inversely proportional to area and proportional to length). Thus, decreasing the thermal conductance of overlayer 44, by, for example, decreasing the cross-sectional area or increasing length of the overlayer metal, may have the opposite effect on electrical resistance (i.e., electrical resistance will increase).

Accordingly, the geometry and composition of overlayer metal will depend upon the particular working surface shape that is employed for the auto-regulating substrate metal, and the intended application of the resulting surgical instrument. For example, in applications where it is not critical to localize the high temperatures in the heating element, for a given geometry it may be desirable to select a material based on its resistivity, rather than its thermal conductivity. Conversely, it may be desirable to trade higher electrical resistance for lower thermal conductance in applications where it is more critical to be able to localize the high temperatures of the heating element.

It will be apparent to one skilled in the art that once the particular application for the surgical instrument has been decided, and the shape and heating requirements of the heating element have been established, the type and geometry of the particular overlayer metal can be determined. These parameters may be chosen either experimentally, for example, by measuring the localization of the heat (i.e., temperature as a function of distance along the surgical instrument), or by a combination of theoretical calculations and experimental measurements. Theoretical estimates may be obtained using conventional macroscopic steady-state equations for electrical resistance (i.e., Electrical Resistance=Resistivity×[Length/Area]) and thermal conductance (i.e., Thermal Conductance=Conductivity× [Area/Length]). Because the heating element is only heated for a few seconds at a time, the transfer of heat from the heating element to the low temperature region 42b may not reach steady-state, however, the use of these theoretical calculations, will for most cases provide adequate estimates of the performance characteristics of the heating element.

Preferably, the thickness of overlayer 44 should be thin enough so that electric current conducts throughout its entire cross-sectional area (i.e., the skin depth is many times its thickness) and thus the electric fields penetrate into the underlying auto-regulating metal substrate.

Overlayer 44 may comprise any metal or alloy that meets the desirable thermal conductance and electrical resistance characteristics requirements discussed above. Overlayer 44 may be disposed on auto-regulating metal substrate 42 using any technique capable of achieving a low electrical resistivity junction and intimate thermal contact with auto-regulating metal substrate 42, such as electroplating. Since plating thickness, produced by electroplating, is normally directly proportional to plating time, it may be advantageous to employ materials requiring thinner thicknesses to reduce the cost of the surgical instrument.

Metals fulfilling the above requirements include, among others, nickel and copper. For the particular embodiment of surgical instrument shown in FIGS. 7–9, and having auto-regulating substrate 42 comprising an 18-mil-thick alloy of iron and nickel, satisfactory performance has been obtained using overlayer 44 of electroplated copper, approximately 0.125 to 0.15 mil thick.

In FIGS. 8A and 8B, an alternative embodiment of a monolithic heating element similar to FIGS. 7A and 7B is described, in which an optional tapered edge 48 is incorporated into heating element 40 to provide thermally-enhanced cutting. Tapered edge 48 is constructed in accordance with the principles hereinbefore discussed with respect to the other embodiments of the heating elements shown in FIGS. 1–6.

Additionally, whether or not a tapered edge 48 has been incorporated into the surgical instrument, heating element 40 may also be provided with a non-stick coating 46 for reducing the accumulation of coagulum on the working surface, as shown in FIGS. 9A and 9B. Non-stick coating 46 is provided in accordance with the principles hereinbefore discussed with respect to the other embodiments of the heating elements shown in FIGS. 1–6. Additionally, in the preferred embodiment, non-stick coating 46 covers high-temperature working surface region 42a completely. Furthermore, if isolation air gap 47 is filled with an alumina cement or other similar material, the non-stick coating may also cover the cement to provide an easy-to-clean surface. As shown in FIGS. 9A and 9B, non-stick coating 46 covers only a portion of low-temperature region 42b (see transition region 41 in FIGS. 9A and 9B). Preferably, transition region 41 is placed inside the shaft which heating element 40 would be disposed from. This reduces the exposure of non-coated material to tissue during surgery.

Thus, it is seen that various embodiments of an instrument for surgery have been provided. The instrument has a heating element with a working surface for providing hemostasis to tissue at an auto-regulated temperature. The working surface may also include a tapered edge for providing thermally-enhanced cutting of tissue, a non-stick coating for operating the instrument at low auto-regulation temperatures, or both. Processes for making such instruments have also been described.

In accordance with an additional aspect of the present invention, it is desirable that surgical instruments with auto-regulating heating elements are powered by a power source (see power source 9 in FIG. 1) that is capable of delivering a selectable and controlled amount of current to the heating element. The use of such selectable and controllable current, in combination with the auto-regulating heating element of the present invention, produces a surgical instrument with substantially stable temperature regulation, even after the activated heating element contacts colder tissue. In use, the high frequency current level is selected to elevate the heating element above it's auto-regulation temperature in the range of the Curie transition of the heating element. As the heating element contacts tissue and cools below the auto-regulation temperature, the skin depth decreases and, under constant current conditions, the amount of resistance heating increases.

A preferred power source capable of delivering a selectable and controllable current is described in commonly-assigned, co-pending U.S. patent application Ser. No. 07/877,454. This power supply is capable of delivering a substantially constant current level.

The method of the present invention, wherein an auto-regulating heating element of a surgical instrument is used in combination with a power source capable of delivering a selectable and controlled amount of current, has been found to be suitable for performing a great variety of surgical procedures on a patient's tissue. This method comprises the steps of:

(a) connecting the instrument to a power source for supplying AC electrical power to the heating element;

(b) disposing the working surface of the instrument adjacent the patient's tissue;

(c) selecting and controllably supplying a current from the power source to the heating element to maintain the working surface substantially at the auto-regulated temperature; and (d) placing the working surface in substantial contact with the patient's tissue so as to transfer heat from the working surface to the patient's tissue.

The above method has provided highly satisfactory performance under a wide range of conditions, working surface geometries and auto-regulation temperatures. In particular, controlled current levels selected in the range of from about 1 to about 10 amperes have provided auto-regulation temperatures from as low as 100° C. to as high as 600° C., depending upon the particular ferromagnetic material selected and the working surface area of the instrument. Additionally, frequencies in the range of from about 400 khz to about 8 Mhz, and more particularly about 1.8 Mhz, have been determined to provide highly satisfactory performance.

The above method, in addition to being able to perform surgery at working surface temperatures in the range of from about 500° to 600° C. (at which no non-stick coating is necessary as coagulum does not adhere at these higher temperatures), allows surgery to be performed at temperatures as low as approximately 100° C. when a non-stick coating is employed on the working surface. The ability of the present invention to be able to perform surgery at such low temperatures can be significant since the generation threshold of "smoke" from heated tissue can occur at temperatures on the order of approximately 290° to 330° C. Because the present invention can provide hemostasis in conjunction with thermally-enhanced cutting during surgery at temperatures in the range of approximately 100° to 300° C., the quality of surgery can be improved since the amount of vision-impairing smoke may be reduced.

Furthermore, there are other advantages of the ability of the present invention to operate at temperatures in the range of approximately 100° to 300° C. Because surgery, e.g., endoscopic surgery, is sometimes performed in the presence of gases which are flammable at temperatures in the range of approximately 300° to 400° C. and above (e.g., internal, patient-generated, methane, and externally-administered oxygen-rich mixtures), the present invention can reduce the chances of igniting such gases, because of the lower temperatures involved, and thus may improve the safety of the patient and surgical staff.

Additionally, since the time it takes to heat the surgical instruments of the present invention under controlled current levels is generally proportional to the operating temperature, reducing the operating temperature from approximately 550° C. to less than 300° C., reduces the heat-up time by a factor of approximately 2 (i.e., from approximately 2 seconds to 1 second).

Thus, in addition to providing an instrument for surgery and a process for making such instrument, the present invention also provides a method wherein a surgical instrument is used in combination with a selectable and controllable amount of current for performing surgical procedures on a patient's tissue.

One skilled in the art will appreciate that the present invention can be practiced by other than the described embodiments, which are presented for purposes of illustration and not of limitation, and the present invention is limited only by the claims which follow.

What is claimed is:

1. An instrument for use in surgery comprising:

a shaft having a proximal end and a distal end;

a working end connected to the distal end of the shaft for manipulating and coagulating tissue, the working end having a working surface for contacting tissue and a cross-section extending perpendicularly to the working surface, the working end integrally formed of a heating element, the working surface maintained at an auto-regulated temperature by conducting a current throughout the entire cross-section of the working end, the heating element comprising a material having a skin depth extending substantially throughout the cross-section of the working end responsive to the temperature of the heating element and that decreases as the temperature of the heating element falls below the auto-regulated temperature;

first and second electrode leads connected to the proximal end of the shaft; and means connecting the first and second electrode leads to the working end.

2. An instrument as defined in claim 1 wherein the material of said heating element further comprises a material that exhibits a Curie transition in permeability.

3. An instrument as defined in claim 2 wherein the material further comprises a ferromagnetic material.

4. An instrument as defined in claim 3 wherein the material further comprises an element selected from the group consisting of iron, nickel and cobalt.

5. An instrument as defined in claim 3 wherein the material further comprises an alloy of iron and nickel.

6. An instrument as defined in claim 5 wherein the alloy further comprises nickel having a concentration in the range of approximately 35 percent to approximately 55 percent by weight.

7. An instrument as defined in claim 1 wherein the working surface further comprises a tapered edge for thermally-enhanced cutting of tissue at a temperature in the range of the auto-regulated temperature, wherein the tapered edge defines an apex having an angle in the range of approximately 15 to approximately 50 degrees.

8. An instrument as defined in claim 1 wherein the working surface further comprises a coating of electrically-insulating non-stick material to reduce the accumulation of coagulum on the working surface.

9. An instrument as defined in claim 1 wherein the shaft has a distal region adjacent to the distal end, the instrument further comprising a heater support member adjacent to the distal end and interposed between the working end and the electrode leads, the heater support member having a low thermal conductance so that conduction of heat from the working end to the distal region of the shaft is reduced.

10. An instrument as defined in claim 9 wherein the heater support member further comprises a material having a low electrical resistance.

11. The instrument as defined in claim 1 in combination with a power source that provides a substantially constant current output to the instrument at a selectable level, the substantially constant current output of the power source substantially independent of the deviation of the working surface temperature from the auto-regulation temperature during surgery.

12. Apparatus as defined in claim 11 wherein the power source has a current level selectable from the range of 1 to 10 amperes.

13. A working end for use in a surgical instrument comprising:

a substrate integrally formed of a heating element and having both a high-temperature working surface region for manipulating and coagulating tissue, and a low-temperature region for disposing the heating element adjacent a distal end of a shaft, the high-temperature working surface region having a working surface and a cross-section extending perpendicularly to the working surface, the working surface maintained at an auto-regulated temperature by conducting a current throughout the entire cross-section, the substrate comprising a material having a skin depth extending throughout the cross-section of the high-temperature working surface region responsive to the temperature of the high-temperature working surface region and that decreases as the temperature of the high-temperature working surface region falls below the auto-regulated temperature; and an overlayer disposed on the low-temperature region of the substrate, the overlayer having a low thermal conductance for reducing the conduction of heat from the high-temperature working surface region to the low-temperature region of the substrate.

14. A working end as defined in claim 13 wherein the overlayer further comprises a material having a low electrical resistance.

15. A working end as defined in claim 14 wherein the material further comprises a ferromagnetic material that exhibits a Curie transition in permeability.

16. A working end as defined in claim 15 wherein the material further comprises an alloy of iron and nickel, wherein the alloy further comprises nickel having a concentration in the range of approximately 35 percent to approximately 55 percent by weight.

17. A working end as defined in claim 13 wherein the substrate has a thickness approximately eight to ten times the skin depth of the substrate at working surface temperatures below the auto-regulation temperature.

18. A working end as defined in claim 13 wherein the working surface further comprises a tapered edge for thermally-enhanced cutting of tissue at a temperature in the range of the auto-regulated temperature.

19. A working end as defined in claim 13 wherein the working surface further comprises a coating of electrically-insulating non-stick material to reduce coagulum accumulation on the working surface.

20. An instrument for use in surgery comprising:

a shaft having a proximal end and a distal end;

a working end connected to the distal end of the shaft for manipulating and hemostatically cutting tissue, the working end having a working surface for contacting tissue and a cross-section extending perpendicularly to the working surface, the working end integrally formed of a heating element, the working surface maintained at an auto-regulated temperature by conducting a current throughout the entire cross-section of the working end, the working surface including an atraumatic edge that becomes capable of cutting tissue when heated to a temperature in the range of the auto-regulated temperature, the heating element comprising a material having a skin depth extending substantially throughout the cross-section of the working end responsive to the temperature of the heating element and that decreases as the temperature of the heating element falls below the auto-regulated temperature;

first and second electrode leads connected to the proximal end of the shaft; and means connecting the first and second electrode leads to the working end.

21. An instrument as defined in claim 20 wherein the material of said heating element further comprises a material that exhibits a Curie transition in permeability.

22. An instrument as defined in claim 21 wherein the material further comprises a ferromagnetic material.

23. An instrument as defined in claim 20 wherein the atraumatic edge comprises a tapered edge defining an apex having an angle in the range of approximately 15 to approximately 50 degrees.

24. An instrument as defined in claim 20 wherein the working surface further comprises a coating of electrically-insulating non-stick material to reduce accumulation of coagulum on the working surface.

25. An instrument as defined in claim 20 wherein the shaft has a distal region adjacent to the distal end, the instrument further comprising a heater support member adjacent to the distal end and interposed between the working end and the electrode leads, the heater support member having a low thermal conductance and low electrical resistance so that conduction of heat from the working end to the distal region of the shaft is reduced.

26. The instrument as defined in claim 20 in combination with a power source that provides a substantially constant current output to the instrument at a selectable level, the substantially constant current output of the power source substantially independent of the deviation of the working surface temperature from the auto-regulation temperature during surgery.

27. Apparatus as defined in claim 26 wherein the power source has a current level selectable from the range of 1 to 10 amperes.

28. A working end for use in a surgical instrument comprising:

a substrate integrally formed of a heating element and having both a high-temperature working surface region for manipulating and hemostatically cutting tissue, and a low-temperature region for disposing the heating element adjacent a distal end of a shaft, the high-temperature working surface region having a working surface and a cross-section extending perpendicularly to the working surface, the working surface maintained at an auto-regulated temperature by conducting a current throughout the entire cross-section, the working surface including an atraumatic edge that becomes capable of cutting tissue when heated to a temperature in the range of the auto-regulated temperature, the substrate comprising a material having a skin depth extending throughout the cross-section of the high-temperature working region responsive to the temperature of the high-temperature working surface region and that decreases as the temperature of the high-temperature working surface region falls below the auto-regulated temperature; and a metallic overlayer disposed on the low-temperature region of the substrate and electrically coupled thereto, the metallic overlayer having a low thermal conductance for reducing the conduction of heat from the high-temperature working surface region to the low-temperature region of the substrate.

29. A working end as defined in claim 28 wherein the material further comprises a ferromagnetic material that exhibits a Curie transition in permeability.

30. A working end as defined in claim 29 wherein the material further comprises an alloy of iron and nickel, wherein the alloy further comprises nickel having a concentration in the range of approximately 35 percent to approximately 55 percent by weight.

31. A working end as defined in claim 28 wherein the substrate has a thickness approximately eight to ten times the skin depth of the substrate at working surface temperatures below the auto-regulation temperature.

32. A working end as defined in claim 28 wherein the atraumatic edge further comprises a tapered edge.

33. A working end as defined in claim 28 wherein the working surface further comprises a coating of electrically-insulating non-stick material to reduce coagulum accumulation on the working surface.

\* \* \* \* \*